(12) United States Patent
Hilbig

(10) Patent No.: US 8,696,795 B2
(45) Date of Patent: Apr. 15, 2014

(54) OXYGEN SEPARATION METHOD AND SYSTEM WITH A PLASMA PUMP AND A MEMBRANE

(75) Inventor: Rainer Hilbig, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/515,525

(22) PCT Filed: Dec. 14, 2010

(86) PCT No.: PCT/IB2010/055787
§ 371 (c)(1),
(2), (4) Date: Jun. 13, 2012

(87) PCT Pub. No.: WO2011/073889
PCT Pub. Date: Jun. 23, 2011

(65) Prior Publication Data
US 2012/0247329 A1   Oct. 4, 2012

(30) Foreign Application Priority Data

Dec. 17, 2009   (EP) ..................................... 09179682

(51) Int. Cl.
*B01D 53/22*   (2006.01)
(52) U.S. Cl.
USPC ..................... 95/54; 95/43; 95/45; 96/4; 96/7
(58) Field of Classification Search
CPC ................. B01D 53/22; B01D 53/228; C01B 2210/0046
USPC .......................... 95/43, 45, 54; 96/4, 7; 417/53
See application file for complete search history.

(56) References Cited

U.S. PATENT DOCUMENTS

| | | | | |
|---|---|---|---|---|
| 4,560,394 A | * | 12/1985 | McDonald et al. | 95/54 |
| 4,834,779 A | * | 5/1989 | Paganessi et al. | 95/44 |
| 4,923,679 A | * | 5/1990 | Fukasawa et al. | 422/48 |
| 5,355,764 A | * | 10/1994 | Marinos et al. | 89/8 |
| 5,753,007 A | | 5/1998 | Russek et al. | |
| 6,667,475 B1 | * | 12/2003 | Parran et al. | 850/9 |
| 7,156,379 B2 | * | 1/2007 | Tanihara et al. | 261/102 |
| 7,166,148 B2 | * | 1/2007 | Lyons et al. | 95/54 |
| 7,258,725 B2 | * | 8/2007 | Ohmi et al. | 95/41 |

(Continued)

FOREIGN PATENT DOCUMENTS

WO   WO2006033896   3/2006

OTHER PUBLICATIONS

Elvers et al. "Ullmann's encyclopedia of industrial chemistry," Cambridge, New York, p. 204, 1990.*

*Primary Examiner* — Jason M Greene
*Assistant Examiner* — Anthony Shumate
(74) *Attorney, Agent, or Firm* — Michael W. Haas

(57) ABSTRACT

The invention relates to a method of separating oxygen from an oxygen containing gas, said method comprising the steps of: compressing and heating the oxygen containing gas in a plasma pump (16), guiding the heated and compressed oxygen containing gas to the primary side of a dense inorganic membrane (58), thereby heating the inorganic membrane by the oxygen containing gas to a temperature at which it is permeable for oxygen, and creating a pressure difference between the primary side and a secondary side of the inorganic membrane (58), wherein an oxygen flow through the inorganic membrane (58) is created, thereby separating the oxygen from the oxygen containing gas.

12 Claims, 2 Drawing Sheets

(56) References Cited

U.S. PATENT DOCUMENTS

| | | | |
|---|---|---|---|
| 7,763,097 B2 * | 7/2010 | Federspiel et al. | 95/46 |
| 2002/0100836 A1 * | 8/2002 | Hunt | 244/50 |
| 2004/0265137 A1 | 12/2004 | Bar-Gadda | |
| 2005/0188748 A1 | 9/2005 | Agarwal et al. | |
| 2012/0177546 A1 * | 7/2012 | Hilbig | 422/305 |
| 2012/0258034 A1 * | 10/2012 | Hilbig et al. | 423/405 |
| 2012/0308779 A1 * | 12/2012 | Klee et al. | 428/158 |
| 2012/0318145 A1 * | 12/2012 | Hilbig et al. | 96/11 |
| 2013/0177657 A1 * | 7/2013 | Hilbig et al. | 424/613 |
| 2013/0213227 A1 * | 8/2013 | Hilbig et al. | 95/54 |

* cited by examiner

OXYGEN SEPARATION METHOD AND SYSTEM WITH A PLASMA PUMP AND A MEMBRANE

FIELD OF THE INVENTION

The invention relates to the field of oxygen separation. More specifically, the invention relates to oxygen separation for therapeutic applications, particularly in the field of home care.

BACKGROUND OF THE INVENTION

Oxygen therapy is the administration of oxygen as a therapeutic modality. It is widely used for a variety of purposes in both chronic and acute patient care as it is essential for cell metabolism, and in turn, tissue oxygenation is essential for all physiological functions. Oxygen therapy should be used to benefit the patient by increasing the supply of oxygen to the lungs and thereby increasing the availability of oxygen to the body tissues, especially when the patient is suffering from hypoxia and/or hypoxaemia. Oxygen therapy may be used both in applications in hospital or in home care. The main home care application of oxygen therapy is for patients with severe chronic obstructive pulmonary disease (COPD).

Oxygen may be administered in a number of ways. A preferable way of oxygen administration is by using a so called on demand generation of oxygen. Referring to this, commercial solutions, so-called oxygen concentrators or separators, respectively, are widely known. These oxygen concentrators mostly separate oxygen from an oxygen containing gas, so that the oxygen is provided on demand, i.e. directly before use. Most known oxygen concentrators require a compressor to compress the oxygen containing gas. Furthermore, oxygen, preferably pure oxygen, has to be generated. Most known oxygen concentrators thus comprise an organic membrane to separate oxygen from the oxygen containing gas.

The major drawbacks of the known oxygen concentrators are a high costs and a limited convenience with respect to noise. Furthermore, undesired constituents of the oxygen containing gas, mostly nitrogen, are adsorbed on the membrane thereby causing the requirement of a so-called swing process by which the adsorbed gas is desorbed from the membrane. During that desorption step, a separation of oxygen is not possible, because of which two membranes are desired which further increases the costs. Apart from that, the compressors are mostly noisy leading to a decreased convenience especially when the oxygen concentrator is used over night. Furthermore, the generated oxygen is non-sterile, because of which a further measure of disinfection is often desired or necessary.

Traditional oxygen concentrators are bulky, heavy and require ongoing maintenance by patients and home care providers. Such devices produce noise and heat. Furthermore, a reduction of cost price (a compressor unit comes up with a significant contribution), of recurrent purchase costs and of servicing is desirable.

DEFINITIONS

The term "dense membrane", as used herein, shall refer to a membrane which is permeable for oxygen but non-permeable for other gases, especially for nitrogen.

The term "oxygen containing gas", as used herein, shall refer to any gas which at least partly comprises oxygen.

The term "primary side" of the membrane, as used herein, shall refer to the side of the membrane being directed towards the plasma pump.

The term "secondary side" of the membrane, as used herein, shall refer to the side of the membrane being directed towards the outlet of the membrane unit.

SUMMARY OF THE INVENTION

It is an object of the invention to provide a method of separating oxygen which is cost-saving, and improves convenience with respect to maintenance and noise.

This object is achieved by a method of separating oxygen from an oxygen containing gas, said method comprising the steps of: compressing and heating the oxygen containing gas in a plasma pump, guiding the heated and compressed oxygen containing gas to the primary side of a dense inorganic membrane, thereby heating the inorganic membrane by the oxygen containing gas to a temperature at which it is permeable for oxygen, and creating a pressure difference between the primary side and a secondary side of the inorganic membrane, wherein an oxygen flow through the inorganic membrane is created, thereby separating the oxygen from the oxygen containing gas.

The present invention is based on the unexpected finding that a combination of heating and compressing an oxygen containing gas in a plasma pump together with separating the oxygen by an inorganic membrane leads to surprising and very beneficial synergistic effects.

By using a plasma pump, the oxygen containing gas is compressed and heated in one step. This leads to the advantage that an additional device for heating the compressed gas or the membrane as such is not required. Contrary thereto, the gas which leaves the plasma pump has a sufficiently high temperature to heat the inorganic membrane thereby enabling a sufficiently high oxygen flow through said membrane. Thus, the generally undesired effect, that, by compressing a gas with a plasma pump, the compressed oxygen containing gas has an elevated temperature, is thus directly very well applicable in combination with an inorganic membrane.

Furthermore, a plasma pump works with a reduction of noise leading to a considerable increase in convenience, especially in home care applications. The convenience is even more improved by the fact that by providing a plasma pump for heating and compressing the oxygen containing gas, the used device has reduced size and weight which is particular advantageous for home care applications.

Additionally, by using an arrangement with both a plasma pump and an inorganic membrane, oxygen is separated with lower costs due to the fact that the arrangement as such may be designed much cheaper, and furthermore, the energy efficiency is improved compared to the methods known from the state of the art.

A further advantage of the method according to the invention is the generation of sterile oxygen. Additional disinfection or sterilization steps are not necessary. According to the invention, an on demand generation of sterile oxygen is provided.

Additionally, swing processes are no longer necessary because nitrogen does not adsorb to the inorganic membrane thereby not limiting the permeability conditions with respect to oxygen.

By using a plasma pump instead of a compressor known from the state of the art an increase with respect to cost price, servicing and noise may thus be achieved.

In a preferred embodiment of the invention, air is used as oxygen containing gas. This is especially preferable at home care applications because no special oxygen containing gases have to be stored.

In a further embodiment, the oxygen containing gas is compressed to a range of ≥2.5 bars to directly come up with an oxygen pressure above atmospheric pressure on the secondary side. This pressure may be enough to get a sufficiently high oxygen flow through the inorganic membrane providing an adequate flow of generated pure oxygen. Referring to this, it is particularly advantageous, if the oxygen containing gas is compressed to a range of 5 bars.

In a further embodiment, the oxygen containing gas is heated to a temperature range of ≥900 K and ≤1300 K. By providing an accordingly heated oxygen containing gas, the inorganic membrane is heated to a sufficiently high temperature to provide adequate permeability properties for oxygen.

In a further embodiment, the oxygen is cooled after separation. This enables a direct administration of oxygen to the patient. The amount of cooling may thereby be adapted to the specific use. In some applications, it is desirable if the oxygen is cooled down to room temperature whereas some applications are more effective when using oxygen at temperatures being elevated with respect to room temperature.

The method according to the invention may be achieved by a gas separation arrangement according to the invention, the arrangement comprising a plasma pump for compressing and heating an oxygen containing gas, and a membrane unit with a dense inorganic membrane, wherein the plasma pump and the membrane unit are connected via a conduct being designed to guide the heated and compressed oxygen containing gas from the plasma pump to the membrane unit, and the dense inorganic membrane being designed to separate oxygen from the oxygen containing gas.

In one embodiment, the inorganic membrane is formed in a tubular shape. This enables a very stable geometry and may further allow the formation of a membrane unit with a decreased size.

In a further embodiment, the arrangement comprises a cooler being arranged downstream the membrane unit. The cooler enables the generated oxygen to be cooled down to a temperature being applicable for direct administration to a patient.

In a further embodiment, a gas reservoir is provided downstream the plasma pump. This enables the formation of a continuous flow of oxygen containing gas and thus of pure oxygen.

In a further embodiment, the inorganic membrane is fixed to a support formed as a porous membrane. This enables a very stable configuration without the requirement of forming the oxygen-selective membrane as such more stable, which reduces costs.

In a further embodiment, a heat isolation is provided outside an inner housing. This enables a better heat efficiency and reduces the required energy input and thus the costs. Here, it is especially preferable, if the heat isolation is designed as a vacuum. This is a special easy and effective way to create a heat isolation.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
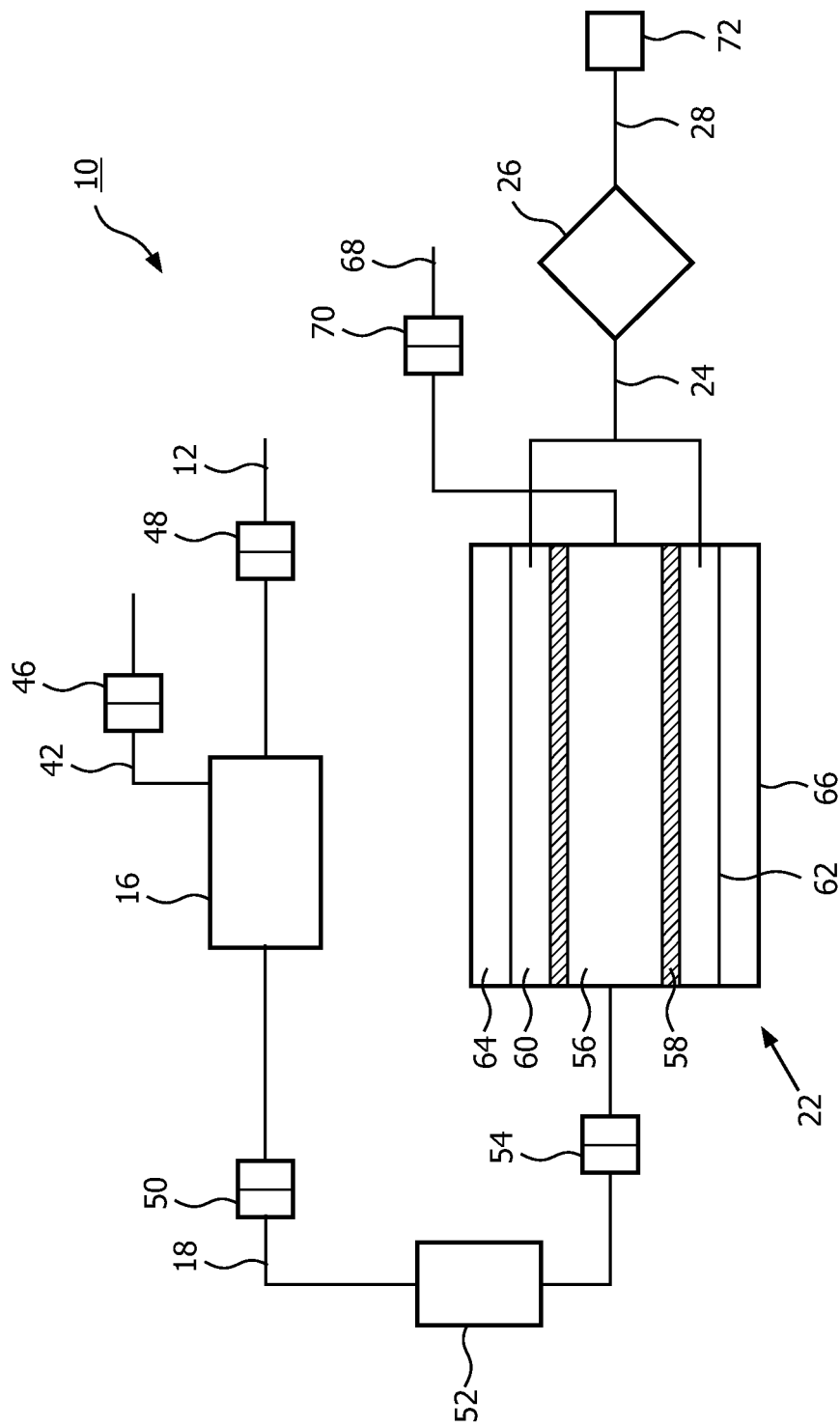
FIG. 1 shows a schematic block diagram of the working principle of the method according to the invention.

In FIG. 1, an arrangement 10 for separating oxygen from an oxygen containing gas is schematically shown. The arrangement 10 is very well suitable for oxygen therapy e.g. in home care applications. However, the arrangement 10 as well as the method according to the invention is not limited to therapeutic applications, but is furthermore suitable for a all kinds of generation of oxygen. As a further exemplary application, it is referred to the oxygen generation in airplanes.

The arrangement 10 comprises a gas inlet 12 for guiding the oxygen containing gas into the arrangement 10. The oxygen containing gas is guided through the gas inlet 12 into a plasma pump 16, and in the following it is entering, through a conduct 18, a membrane unit 22 for separating oxygen. Downstream the membrane unit 22, a conduct 24 may guide the generated pure oxygen to a cooler 26 downstream of which an outlet 28 is provided for administration of the oxygen. The arrangement 10 is described in more detail below.

Figure 2:
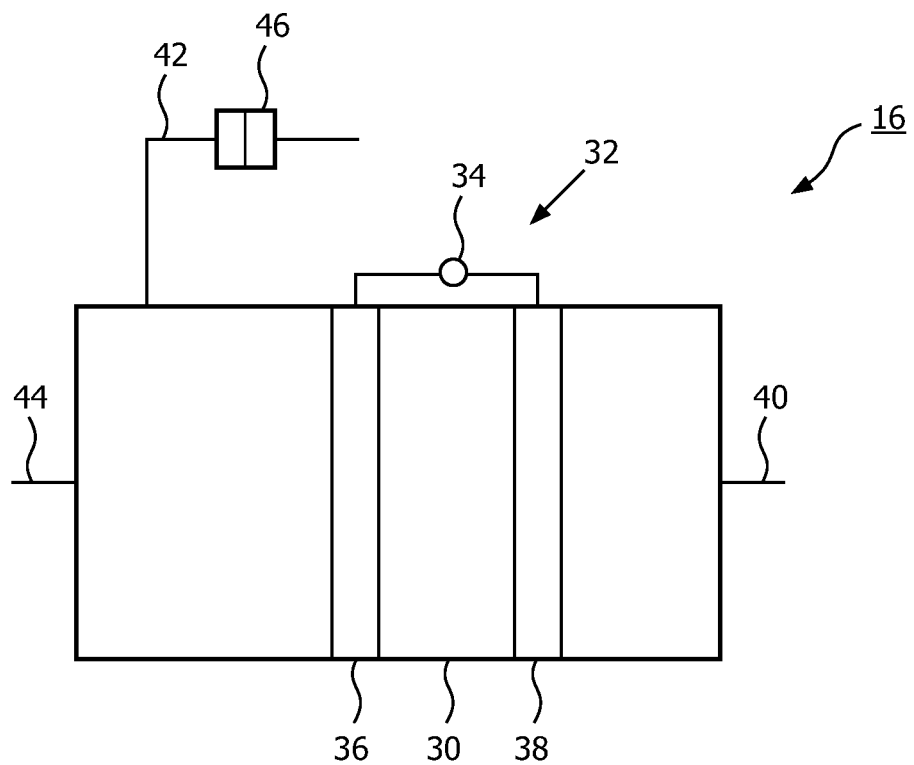
FIG. 2 shows a schematic cross sectional view of a plasma pump according to the invention.

The gas inlet 12 guides the oxygen containing gas into a power-modulated gas discharge compression unit, i.e. a plasma pump 16. An exemplary plasma pump 16, which is well suitable for a method according to the invention, is shown in more detail in FIG. 2.

The plasma pump 16 may comprise a discharge chamber 30 with a gas discharge device 32 for generating a gas discharge inside the discharge chamber 30. The gas discharge device 32 may comprise a coupling device to generate a gas discharge by capacitive, inductive, surface wave and/or microwave coupling, and an energy source 34 to provide the coupling device with an alternating current. The coupling device may comprise two electrodes 36, 38, which are arranged outside the gas discharge chamber 30 for capacitive coupling and which may be formed of carbon. It is preferred, that the coupling device is arranged outside the gas discharge chamber 30. The wearing down of parts of the coupling device, especially of electrodes 36, 38, can be significantly reduced. However, it is also possible to arrange parts of the coupling device at least partially inside the discharge chamber. By means of the energy source 34, a voltage could be applied between the two electrodes 36, 38, leading to a gas discharge and to the generation of a plasma inside the discharge chamber 30. An alternating current allows to sustain the plasma over time, by changing of the amplitude of the alternating current the power of the plasma can be modulated.

The discharge chamber 30 further comprises a gas inlet 40, a first gas outlet 42 and a second gas outlet 44. The gas inlet 40 of the plasma pump 16 is connected to the gas inlet 12 of the arrangement 10. The first gas outlet 42 may further comprise an exhaust device 46 which may be designed as a simple two way valve. It is on one side connected to the discharge chamber 30 and on the other side connected to the atmosphere or a reservoir for exhaust gas.

The discharge chamber 30 is further connected to the second gas outlet 44 which in turn is connected to the conduct 18. To control gas flow through the gas inlet 40 and the second gas outlet 44, an inlet valve 48 is connected with the gas inlet 40 and an outlet valve 50 is connected with the second gas outlet 44 (see FIG. 1). As inlet valve 48 and outlet valve 50, non-return valves or two-way valves can be used, for example. Non-return valves are preferred because they do not need controlling. By adapting the operation of the inlet valve 48 and the outlet valve 50 to a power modulated gas discharge, a gas flow can be generated with a specific direction.

By generating a plasma in the discharge chamber 30 like described above, a pressurized oxygen containing gas is generated. A pressure in the discharge chamber 30 can be increased during high power-operation of the plasma, and the pressure can be decreased during low power operation or turning off the plasma. A pressure swing can be obtained by running a power-modulated discharge in the discharge chamber 30.

In the following, the operation of the plasma pump 16 will be described in more detail in an exemplary manner.

In a first step, it is started at approximately atmospheric pressure, for example 1 bar, and at approximately room temperature, for example 300 K, with closed exhaust device 46, inlet valve 48 and outlet valve 50. A high-power plasma inside the discharge chamber is generated and sustained leading to an increased temperature. Due to the fact that the discharge chamber is closed against the surrounding air, the oxygen containing gas in the discharge chamber of the plasma pump 16 is compressed. Exemplarily, the pressure may thus be increased up to a value of 3 bars due to an increasing temperature of the gas up to a temperature of 900 K caused by the plasma. By opening the outlet valve 50, the oxygen containing gas in the discharge chamber 30 can only leave the chamber 30 by flowing in the conduct 18, thereby causing a constant pressure at further elevated temperatures up to a range of 2100 K in the discharge chamber 30. After a certain interval, in a third step, the gas exhaust device 46 may be opened to the surrounding air. During this phase, the pressure in the discharge chamber 30 goes down to atmospheric pressure and the temperature is increased to a temperature of approximately 1550 K. After a certain interval, the discharge power is reduced significantly or is switched of leading to the gas temperature dropping to approximately room temperature, e.g. 300 K. Fresh oxygen containing gas may now flow into the discharge chamber 30 through the gas inlet 12 and the inlet 40.

After a further time interval, the cycle is finished. For continuing, the plasma pump 16 starts again with the first step. If the plasma has not been switched off, igniting the plasma in the following step can be omitted.

The plasma pump 16 can be operated without an overlapping of the respective steps. Alternatively, the plasma pump 16 can be operated with one or more steps overlapping.

The gas temperatures during burning the plasma may be very high, like described above. Even though there is a temperature distribution leading to the walls of the plasma pump 16 having temperatures being decreased with respect to the central axis, the use of temperature stable materials like quartz glass or aluminum oxides as wall materials of the plasma pump are advantageous.

Generally, a rather small energy input for the plasma pump 16 is sufficient. In detail, a power input of 100 W to 350 W may be sufficient depending on the temperature and membrane conditions. This range of power input is very well suitable for home care applications.

The energy source 34 may deliver a square wave current I at 300 Hz frequency with variable output power, i.e. the root mean square (rms) value of the current $I_{mean}$ at 300 Hz driving frequency can be varied on a time scale above t=50 ms. Currents $I_{mean}$ up to several amperes and powers of several hundred watts are feasible with the electronic driver. The energy source 10 also delivers peak voltages of up to 20 kV for start phase to obtain a gas breakdown/igniting the plasma.

Working in the described cycle, the plasma pump 16 functions as a gas pump. Although the plasma pump 16 woks in different cycles, it may generate a direct and continuous flow of oxygen containing gas due to a high frequency of the working cycles.

To further support a continuous flow, it is preferable to provide a gas reservoir 52 downstream the outlet valve 50. By pressing oxygen containing gas from the discharge chamber 30 inside the gas reservoir 52, an over pressure inside the reservoir 52 can be generated, preferably by increasing the flow resistance downstream the gas reservoir by providing a reservoir valve 54 or, alternatively, an orifice. A constant or nearly constant over pressure can be used to generate a continuous or nearly continuous flow of the oxygen containing gas in the conduct 18.

Downstream the plasma pump 16 or the reservoir 52, respectively, the oxygen containing gas is guided to the membrane unit 22. Upstream the membrane unit 22, a a valve may be provided, which may be the reservoir valve 54 or an additional valve. This valve may close the conduct 18, when the pressure of the oxygen containing gas is insufficient. Contrary thereto, the valve may open the conduct 18 when a sufficiently high pressure is reached. Thus, it may be provided that at a pressure of ≥2.5 bars, in particular at 5 bars, the valve opens, and thus guiding the oxygen containing gas to the membrane unit 22.

Figure 3:
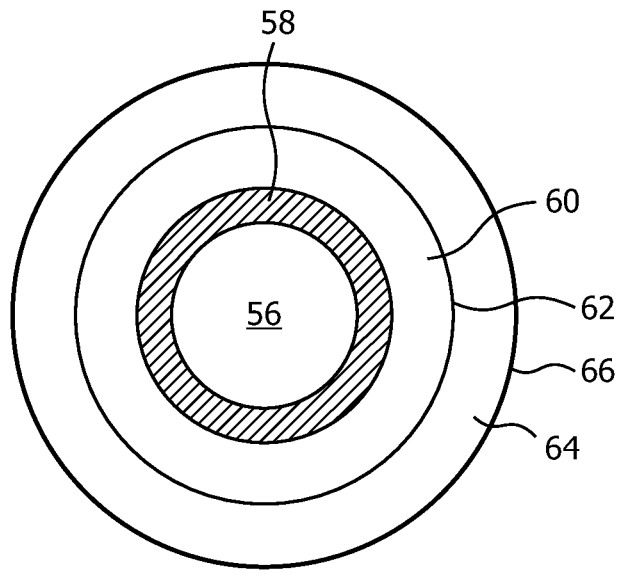
FIG. 3 shows a schematic cross sectional view of a membrane unit according to the invention.

FIG. 3 shows a cross sectional view of the membrane unit 22. The membrane unit 22 may be of any configuration. However, a tubular shape of the membrane unit 22 is especially advantageous. At its inside, the membrane unit 22 comprises an inner conduct 56 being in flow connection with the conduct 18, and allowing the oxygen containing gas to enter the membrane unit 22. The inner conduct 56 is limited at its outside by an inorganic membrane 58, the inorganic membrane 58 having a primary and a secondary side. The primary side is directed to the inner conduct 56 and thus to the plasma pump 16, whereas the secondary side is directed to an outer conduct 60. The outer conduct 60 is limited at its inner side by the inorganic membrane 58 and at its outer side by an inner housing 62. The inner housing 62 may be a tube made from a material being resistant against higher temperatures, for example quartz glass or ceramic aluminum oxide. The objective of the outer conduct 60 is to conduct the separated oxygen out of the membrane unit 22 and is thus in flow connection with the conduct 24. Outside the inner housing 60, a heat isolation 64 is provided. This may preferably be a vacuum, which is provided between the inner housing 62 and an outer housing 66. It is as well possible to provide an inert gas between the inner housing 62 and the outer housing 66. In this case, it would be preferable to provide a very short distance between the inner housing 62 and the outer housing 66 to achieve a sufficient isolation. However, the isolation 64 may be of any kind known from the state of the art to get a sufficient isolation effect. The outer housing 66 may be designed as a thermal shield, for example based on aluminum, to further improve the isolation. This in fact improves the energy efficiency of the arrangement 10 and is thus cost saving.

Referring back to the inorganic membrane 58, its objective is to separate the oxygen from the remaining retentate flow, i.e. the remaining constituents of the oxygen containing gas, and thus to provide a flow of oxygen, which advantageously is a flow of 100% pure oxygen. Mostly, the main remaining constituent is nitrogen, especially in the case when air is used as oxygen containing gas. To get sufficient separation results, it is thus essential that the inorganic membrane 58 is very dense. A dense inorganic membrane 58 is a membrane being is permeable with respect to oxygen, but being strictly or at least substantially non-permeable for other gases, especially for nitrogen.

To achieve these properties, the inorganic membrane 58 may be a solid ceramic membrane comprising selected inorganic oxide compounds. Preferable inorganic membranes are mainly based on a Perovskite or Fluorite crystal structure. As an example, the Perovskite-related material $Ba_{0.5}Sr_{0.5}Co_{0.5}Fe_{0.2}O_{3-\delta}$ (BSCF) is very well suited. It is a general property of these kinds of inorganic membranes that they are completely impervious to all gases at room temperature, but allow oxygen molecules to pass through when heated to elevated temperatures. Mainly, temperatures above 700 K are necessary to achieve a good oxygen flow with the requirement of only small sized membranes. For example, the above named BSCF may come up with an oxygen flow of 13 $ml/cm^2 min$ at 1275 K, wherein a membrane thickness of only 0.2 mm is sufficient.

The inorganic membranes may be either pure oxygen conducting membranes or mixed ionic-electronic conducting membranes. Generally, a force has to be applied to cause the oxygen being transferred through the membrane. This may either be an electronic force. However, it is preferred, that the oxygen passes the inorganic membrane 58 due to a pressure difference between the primary and the secondary side of the inorganic membrane 58.

The compression of the oxygen containing gas in the plasma pump 16 at the same time leads to a pressure difference between the primary side and the secondary side of the inorganic membrane 58. Due to this effect, an increased oxygen partial-pressure at the primary side is generated enabling an oxygen flow through, or a transfer across the dense inorganic membrane 58, respectively. This flow may further be enhanced by providing a reduced pressure on the secondary side of the inorganic membrane 58 instead of an increased pressure at the primary side of the inorganic membrane 58 or additionally thereto. Under extreme conditions, a vacuum may be provided on the secondary side of the inorganic membrane 58 to provide a sufficiently high oxygen flow through the membrane 58.

Without using a reduced pressure on the secondary side, it is preferable to use pressures of ≥2.5 bars upstream the inorganic membrane 58, thus on its primary side. Here, it is especially preferable to use pressures lying in the range of 5 or ≤5 bars. Depending from the temperature of the inorganic membrane 58 and the dimensions of the latter, an oxygen flow with a modest elevation compared to atmospheric pressure, approximately 1 bar, may be achieved at the outlet 28. This may achieved with a pressure of the oxygen containing gas being sensibly reduced with respect to the state of the art. The pressure range according to the invention is especially suitable for home care applications.

It is apparent, that the inorganic membrane 58 has to be stable enough to stand these conditions like described above. This is especially important, as it is preferred to form the inorganic membrane 58 in a very small size or thickness. Especially, by providing an extensive pressure gradient between the primary side and the secondary side of the inorganic membrane 58, it may be advantageous to fix the inorganic membrane 58 on a support. The support may be formed as a porous membrane, in particular a thick inorganic membrane like used for coarse filters. A porous membrane as referred to in this case is a membrane being permeable for gases and non-selective with respect to oxygen. This enables an enhanced stability of the inorganic membrane 58 without the requirement of forming the inorganic membrane 58 as such more stable. This further reduces costs, as the stable and forming component is the membrane support, which is much cheaper than the inorganic membrane 58.

Like stated above, it is essential to heat the inorganic membrane 58 to get sufficient oxygen permeability. According to the invention, this is achieved in an easy and simple way. Due to the provision of a plasma pump 16 for compressing the oxygen containing gas, the compressed gas at the same time is heated to a temperature range being sufficiently high to heat the inorganic membrane 58 to its operational temperature. Exemplary temperature ranges are temperatures ≥700K. It is especially preferable to heat the oxygen containing gas and thus the inorganic membrane to ranges of ≥900K to ≤1300K. In these temperature ranges, very suitable oxygen flows may be achieved.

The combination of a plasma pump 16 to compress and heat the oxygen containing gas together with an inorganic membrane 58 to separate the oxygen from the remaining retentate flow thus improves the energy efficiency of the arrangement 10. It is not necessary to provide a further means for heating the oxygen containing gas and thus the inorganic membrane. This makes an arrangement 10 according to the invention cost-reducing and furthermore enhances size and weight properties, which is especially advantageous for home care applications. Furthermore, the arrangement is kind of "self-cleaning" as due to the high temperatures generated in the plasma pump 16, the oxygen containing gas is sterilized. This has the further advantage of the generated oxygen being sterile, which is preferable for a great amount of applications.

Referring back to FIG. 1, the membrane unit 22 furthermore comprises an outlet 68 which is connected on the one side to the inner conduct 56 and on the other side may be connected to the atmosphere. Through the outlet 68, gas with reduced oxygen content, especially nitrogen, leaves the membrane unit 22. This is the exhaust gas of the membrane unit 22. The outlet 68 may comprise a further valve 70, which is especially advantageous, if a pressure is provided inside the inner conduct 56.

Downstream the membrane unit 22, the conduct 24, which may comprise a further valve like a non return valve, is connected to an outlet 28. The outlet 28 may be equipped with mouthpiece 72 or the like, enabling a direct administration of the generated oxygen. Thus, an additional valve or a small compressor may be provided for a sufficient flow of pure oxygen. Downstream the conduct 24, but upstream the outlet 28, a cooler 26 may optionally be provided. The cooling of cooler 26 may be done by a forced air stream using the surrounding air—(using a ventilator or the like). It may be necessary as the oxygen is still in elevated temperatures downstream the inorganic membrane 58 and it is advantageous for a great amount of applications to cool down the generated oxygen, in an exemplary case, to room temperature. However, it might be advantageous, not to cool down the oxygen, because some oxygen based therapies are more efficient by using oxygen with elevated temperatures.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to

The invention claimed is:

1. Method of separating oxygen from an oxygen containing gas, said method comprising the steps of:
   compressing and heating the oxygen containing gas in a plasma pump;
   guiding the heated and compressed oxygen containing gas to the primary side of a dense inorganic membrane;
   heating the inorganic membrane by the oxygen containing gas to a temperature at which it is permeable for oxygen; and
   creating a pressure difference between the primary side and a secondary side of the inorganic membrane, wherein an oxygen flow through the inorganic membrane is created, thereby separating the oxygen from the oxygen containing gas.

2. Method according to claim 1, wherein air is used as oxygen containing gas.

3. Method according to claim 1, wherein the oxygen containing gas is compressed to a range of ≥2.5 bars, in particular to a range of ≥2.5 bars and ≤5 bars such that the oxygen pressure on the secondary side of the inorganic membrane is above atmospheric pressure during the flow of oxygen through the inorganic membrane.

4. Method according to claim 1, wherein the oxygen containing gas is heated to a temperature range of ≥900 K and ≤1300 K.

5. Method according to claim 1, wherein the oxygen is cooled after separation.

6. Oxygen separating arrangement, comprising:
   a plasma pump for compressing and heating an oxygen containing gas, and
   a membrane unit with a dense inorganic membrane, wherein
   the plasma pump and the membrane unit are connected via a conduct being designed to guide the heated and compressed oxygen containing gas from the plasma pump to the membrane unit, and wherein
   the dense inorganic membrane is designed to separate oxygen from the oxygen containing gas.

7. Arrangement according to claim 6, wherein the inorganic membrane is formed in a tubular shape.

8. Arrangement according to claim 6, wherein the arrangement comprises a cooler being arranged downstream the membrane unit.

9. Arrangement according to claim 6, wherein a gas reservoir is provided downstream the plasma pump.

10. Arrangement according to claim 6, wherein the inorganic membrane is fixed to a support formed as a porous membrane.

11. Arrangement according to claim 6, wherein a heat isolation is provided outside a housing for the inorganic membrane.

12. Arrangement according to claim 11, wherein the heat isolation is a vacuum formed between the housing and an outer housing surrounding the housing.

* * * * *